United States Patent
Jourdain et al.

(10) Patent No.: US 6,541,964 B1
(45) Date of Patent: Apr. 1, 2003

(54) METHOD AND APPARATUS FOR DETERMINING HYDRIDE CONTENT IN A MEASUREMENT OBJECT

(75) Inventors: Pascal Jourdain, Västerås (SE); Kurt-Åke Magnusson, Skultuna (SE)

(73) Assignee: Westinghouse Atom AB, Västerås (SE)

( * ) Notice: Subject to any disclaimer, the term of this patent is extended or adjusted under 35 U.S.C. 154(b) by 0 days.

(21) Appl. No.: 09/831,943
(22) PCT Filed: Nov. 26, 1999
(86) PCT No.: PCT/SE99/02209
§ 371 (c)(1), (2), (4) Date: Jun. 27, 2001
(87) PCT Pub. No.: WO00/34768
PCT Pub. Date: Jun. 15, 2000

(30) Foreign Application Priority Data

Nov. 26, 1998 (SE) .................................. 9804079

(51) Int. Cl.$^7$ .................... G01N 27/90; G01R 33/12
(52) U.S. Cl. .................... 324/232; 324/239; 324/236
(58) Field of Search ................... 324/234, 236, 324/232, 239, 262

(56) References Cited

U.S. PATENT DOCUMENTS

| | | |
|---|---|---|
| 4,107,605 A | 8/1978 | Hudgell |
| 4,593,245 A | 6/1986 | Viertl |
| 4,706,020 A | 11/1987 | Viertl |
| 5,017,869 A | 5/1991 | Oliver |
| 5,402,098 A | 3/1995 | Ohta et al. |
| 5,889,401 A | 3/1999 | Jourdain et al. |

FOREIGN PATENT DOCUMENTS

| | | |
|---|---|---|
| EP | 0506362 | 9/1992 |
| GB | 2187844 | 9/1987 |
| SU | 1185217 | 10/1985 |
| SU | 1610420 | 11/1990 |

OTHER PUBLICATIONS

WPI/Derwent's abstract, Accession No. 98–484336, week 9842, Abstract of JP 10206394 (Hitachi Engineering Co. Ltd.), Aug. 7, 1998.

*Primary Examiner*—Walter E. Snow
(74) *Attorney, Agent, or Firm*—Swidler Berlin Shereff Friedman, LLP

(57) ABSTRACT

The invention concerns a method and apparatus for determining the hydride content in an electrically conductive substrate by generating a first electromagnetic alternating field that at least partly penetrates the substrate which in turn produces a second alternating field that reacts with the first field. The first field is set at at least two different frequencies and measurement at the frequencies of the combined alternating field formed by the interaction of the first and second fields determines the hydride content in the substrate.

14 Claims, 7 Drawing Sheets

METHOD AND APPARATUS FOR DETERMINING HYDRIDE CONTENT IN A MEASUREMENT OBJECT

BACKGROUND OF THE INVENTION AND PRIOR ART

Figure 1:
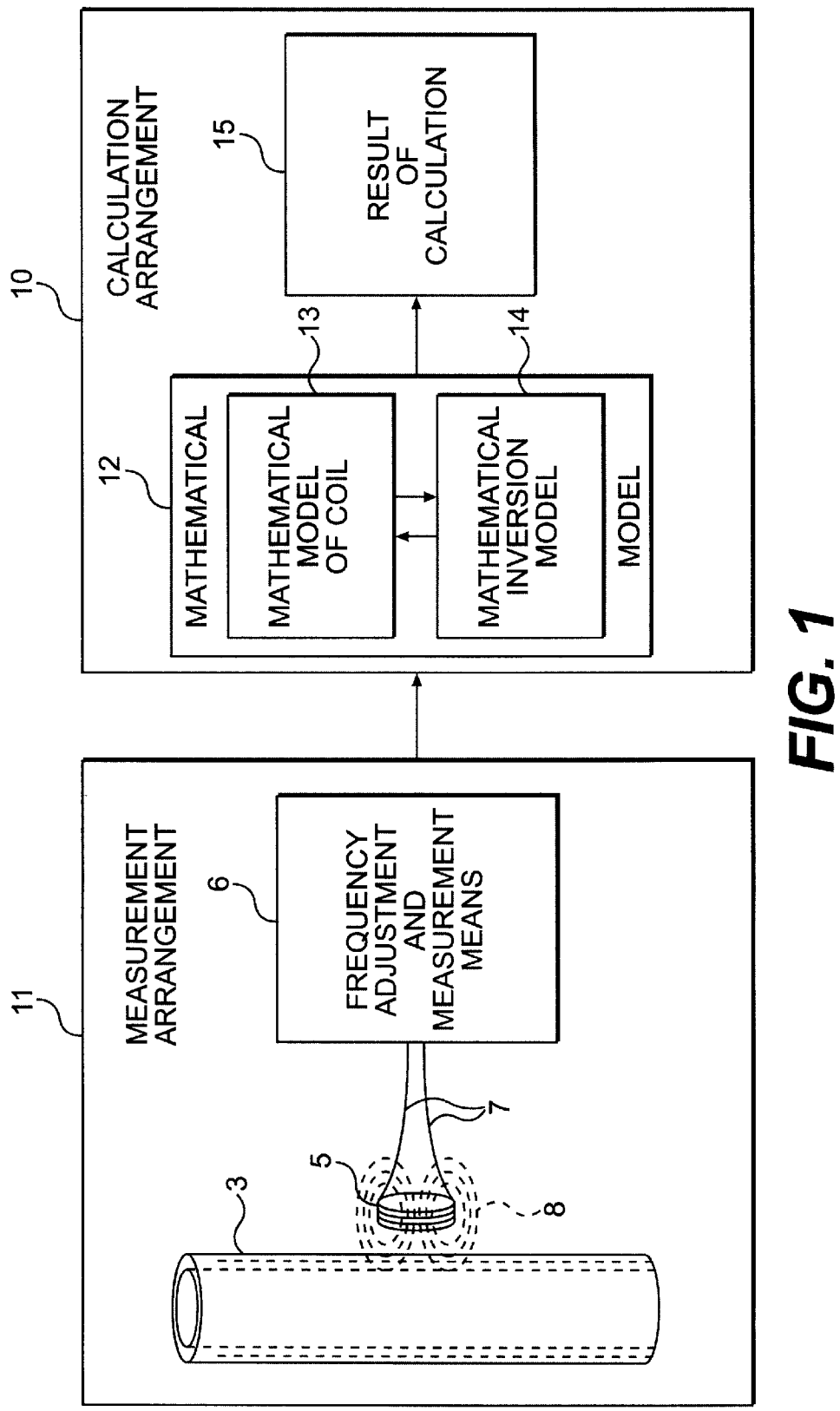

The present invention concerns a method for determining, inter alia, the hydride content in a measurement object by means of an inductive eddy current method. Methods and device for determining layer thickness by means of eddy currents are known through U.S. Pat. No. 5,017,869 and UK-A-2187844.

The published Swedish patent application 9602658-8 (and the corresponding U.S. patent application Ser. No. 08/679 624, Jourdain et al) describes a method and a device for determining the thickness of one or more layers arranged on each other on a substrate, wherein at least one of the layers or the substrate is electrically conductive. According to this method (and device) an electromagnetic alternating field is generated in the immediate vicinity of the outermost layer such that this field generates eddy currents in said electrically conductive layer, which eddy currents retroact on this field, and the influence of the eddy currents on the alternating field is measured and the thickness of the layer or layers is determined based on this measurement. Said measurement is performed in that the frequency of the alternating field is set at at least two different values and the alternating field resulting from said retroaction is measured at these frequency values, wherein the thickness of the layer or layers is calculated on the basis of data obtained through the last mentioned measurement and information about at least some of the electromagnetic properties of the substrate and the layer or layers.

A method and a device of this kind may be used for measuring the thickness of one or more layers within different technical fields.

Said Swedish patent application describes primarily the use of such a method and of such a device for measuring the thickness of layers which are formed on substrates in the form of fuel rods in nuclear power reactors. Such fuel rods are usually formed by a zirconium alloy and comprise the fuel itself, usually in the form of a number of small sintered pellets of uranium dioxide. In the very reactive environment in which these fuel rods are located, a number of chemical reactions occur, of which one is that a layer of zirconium dioxide is formed on the zirconium alloy itself, wherein this layer grows inwards. This has as a consequence that the thickness of the substrate gradually decreases at the same time as the thickness of the oxide layer increases. Furthermore, a so-called crud layer is formed on the oxide layer. This layer usually consists of a mixture of Fe, Zn and O. Since the substrate is electrically conductive, when it consists of said zirconium alloy, the mentioned method may be used for determining the thickness of the oxide layer. It is the case that the eddy currents which are produced by the alternating field in the electrically conductive substrate will interfere with the alternating field itself, wherein this interference decreases with the distance between the coil and the substrate, i.e. with the thickness of the oxide layer and a possible crud layer position thereon. By the method and the device which are described in said Swedish patent application, it has been shown that a very good determination of layer thicknesses may be obtained.

Within different fields there may be a problem in that hydrogen penetrates into a material and changes the properties of the material. One case where hydrogen may impair the properties of a material is in a nuclear plant. For example, the cladding tubes of fuel rods in such a plant are, as has been mentioned, often produced in a zirconium alloy. In this zirconium alloy, hydrogen may penetrate and combine with zirconium to form zirconium hydride. This makes the material more fragile and more brittle. There is therefore a limit for how much hydrides may be permitted without the material becoming too brittle. The measurement of how much hydride there is in a substrate is particularly difficult if there may be one or more layers on the substrate, which is the case for example in connection with cladding tubes for fuel rods in a nuclear plant.

In order to measure the hydride content in the fuel rods it has previously been necessary to remove the fuel rods from the nuclear plant and to measure at another location. This procedure is complicated and expensive. It would therefore be desirable to find a simplified and improved method and device for measuring the hydride content of an electrically conductive substrate of a measurement object which also may have one or more layers positioned on the substrate.

SUMMARY OF THE PRESENT INVENTION

The inventors of the present invention have surprisingly arrived at the fact that the method (and device) for measuring layer thicknesses which is described in the above-mentioned document, may be developed in order to also measure hydride content. The invention may be applied in any field where it is desirable to determine the hydride content in a substrate which may have one or more layers positioned on the substrate.

A method according to the invention for determining the hydride content in an electrically conductive substrate of a measurement object comprises the following steps:

generation of a first electromagnetic alternating field in the immediate vicinity of the measurement object, wherein the electromagnetic alternating field is such that it at least partly penetrates the substrate and in this substrate creates eddy currents which in their turn produce a second electromagnetic alternating field which retroacts on the first electromagnetic alternating field;

setting of the first electromagnetic alternating field at at least two different frequencies;

measurement at said frequencies of the combined electromagnetic alternating field which is formed by the interaction of the first and the second electromagnetic alternating fields; and determination of the hydride content in the substrate by using data which have been obtained through said measurement and information about at least some of the electromagnetic properties of the measurement object.

According to an embodiment of the invention, said determination is done by means of a model, which describes a coil for the generation of the first electromagnetic alternating field and the constitution of the measurement object and the influence of the measurement object on the first electromagnetic alternating field generated by the coil. By using such a model, it has been shown that a good result in the determination of the hydride content may be achieved in a relatively simple manner. It should be noted that the model of the coil may be a simplified model where the coil for example is described as if it comprised a single turn of winding, or as if it comprised several turns of winding positioned in a plane.

According to another embodiment of the invention, the measurement object comprises at least one layer positioned on the substrate, wherein said determination comprises a calculation of a resulting combined electromagnetic alternating field, which calculation comprises the introduction of predetermined or known values for at least some of the electromagnetic properties of the substrate and/or layer or layers and the assumption of one or more free parameters, such as the electric conductivity of the substrate and the thickness of the layer or layers positioned on the substrate, and wherein said determination comprises an iterative process according to which the assumed free parameter or parameters are changed until the measured combined electromagnetic field corresponds to the is calculated field. By such an iterative process and such a calculation, it is possible to in a relatively simple manner arrive at the hydride content even if several unknown parameters have to be assumed in the determination.

According to another embodiment of the invention, the method also comprises the determination of the thickness of at least one layer positioned on the substrate, which determination comprises the use of data which have been obtained through said measurement and information about at least some of the electromagnetic properties of the substrate or the layers. It is an important advantage with the present invention that both the thickness of one or more layers positioned on the substrate and the hydride content in the substrate may be determined.

Still another embodiment of the invention comprises determination of the electric conductivity of the substrate, wherein from this determination the hydride content is determined. By first determining the electric conductivity, the hydride content may then be determined in a relatively simple manner.

The method according to the invention is particularly suited to be used in connection with a measurement object which comprises a structural element in a nuclear plant, wherein said substrate may be the material of the structural member and wherein there may be an oxide layer and a crud layer on said substrate. An example of such a structural element is as has been mentioned cladding tubes for the fuel rods. It may however be of interest to measure the hydride content also on other structural elements which are used in the reactive environment in a nuclear reactor. Such other structural elements comprise spacers, which, inter alia, hold the fuel rods at determined distances from each other, and casing tubes, so-called box walls, which surround a fuel assembly.

In order to achieve a good inductive coupling with the measurement object, the first electromagnetic alternating field in suitably generated by means of a coil which is positioned in the immediate vicinity of the measurement object.

According to still another embodiment of the invention, said coil is formed by an electrically conductive material and comprises at least a first spiral-shaped part which along essentially its full length is tangent to an essentially plane boundary surface. It has been shown that by such a coil, formed with a spiral-shaped part, a very high resolution may be obtained even when the measurement is done on a substrate with a coating of thin layers.

It has been shown to be advantageous if the measurements of the alternating field are performed over a wide frequency range extending over one or more orders of magnitude. Said frequency range may for example cover the frequencies between 500 kHz and 50 MHz.

A device according to the invention for determining the hydride content in an electrically conductive substrate of a measurement object comprises means for generating such a first electromagnetic alternating field in the immediate vicinity of the measurement object that this alternating field at least partly penetrates the substrate and in this substrate creates eddy currents which in their turn produce a second electromagnetic alternating field which retroacts on the first electromagnetic alternating field;

means for setting the first electromagnetic alternating field at at least two different frequencies;

means for measuring, at said frequencies, the combined electromagnetic alternating field which is formed by the interaction of the first and the second electromagnetic alternating fields; and an arrangement arranged for determining the hydride content in the substrate by using data, which have been obtained through said measurement and information about at least some of the electromagnetic properties of the measurement object.

According to an embodiment of the device, said arrangement is arranged such that said determination is performed by means of a model which describes a coil for the generation of the first electromagnetic alternating field and the constitution of the measurement object and the influence of the measurement object on the first electromagnetic alternating field generated by the coil.

According to a further embodiment of the device, said arrangement has means for introducing predetermined or known values for at least some of the electromagnetic properties of the substrate and of on the substrate positioned layers, and means for introducing one or more free parameters, such as the electric conductivity of the substrate and the thickness of the layer or layers positioned on the substrate, wherein said arrangement is arranged such that said determination comprises a calculation of a resulting combined electromagnetic alternating field, which calculation uses the introduced predetermined or known values and the free parameters, and wherein the arrangement is arranged such that said determination comprises an iterative process according to which the assumed free parameter or parameters are changed until the measured combined electromagnetic field corresponds to the calculated field.

According to still another embodiment of the device, the arrangement is arranged such that also the thickness of at least one layer positioned on the substrate is determined by using data which have been obtained through said measurement and information about at least some of the electromagnetic properties of the substrate or the layers.

According to still another embodiment of the device, the arrangement is arranged such that the electric conductivity of the substrate is determined and such that from this determination the hydride content is determined.

According to an advantageous embodiment of the device, the device comprises a coil for generating said first electromagnetic alternating field. Said coil in formed of an electrically conductive material and comprises suitably at least a first spiral-shaped part which along essentially its full length is tangent to an essentially plane boundary surface.

The device may suitably be arranged such that the measurements of the alternating field are performed over a wide frequency range extending over one or more orders of magnitude.

The different embodiments of the device have advantages corresponding to those which have been described in connection with the embodiments of the method above Concerning both the method and the device, the measurement is thus done at at least two different frequencies, for example at three or more different frequencies, preferably at five or more different frequencies. It has thus been shown that a good accuracy may be achieved if the measurement is done at several different frequencies.

It should also be noted that the present invention in useful whenever the hydride content is to be measured in different materials. Examples of such materials are zirconium alloys and hafnium alloys.

SHORT DESCRIPTION OF THE DRAWINGS

Here below a preferred embodiment of the invention given as example will be described with reference to the annexed drawings. It should be noted that FIGS. 1–5 show the principle for measuring layer thickness according to the above-mentioned Swedish patent application.

Figure 2:
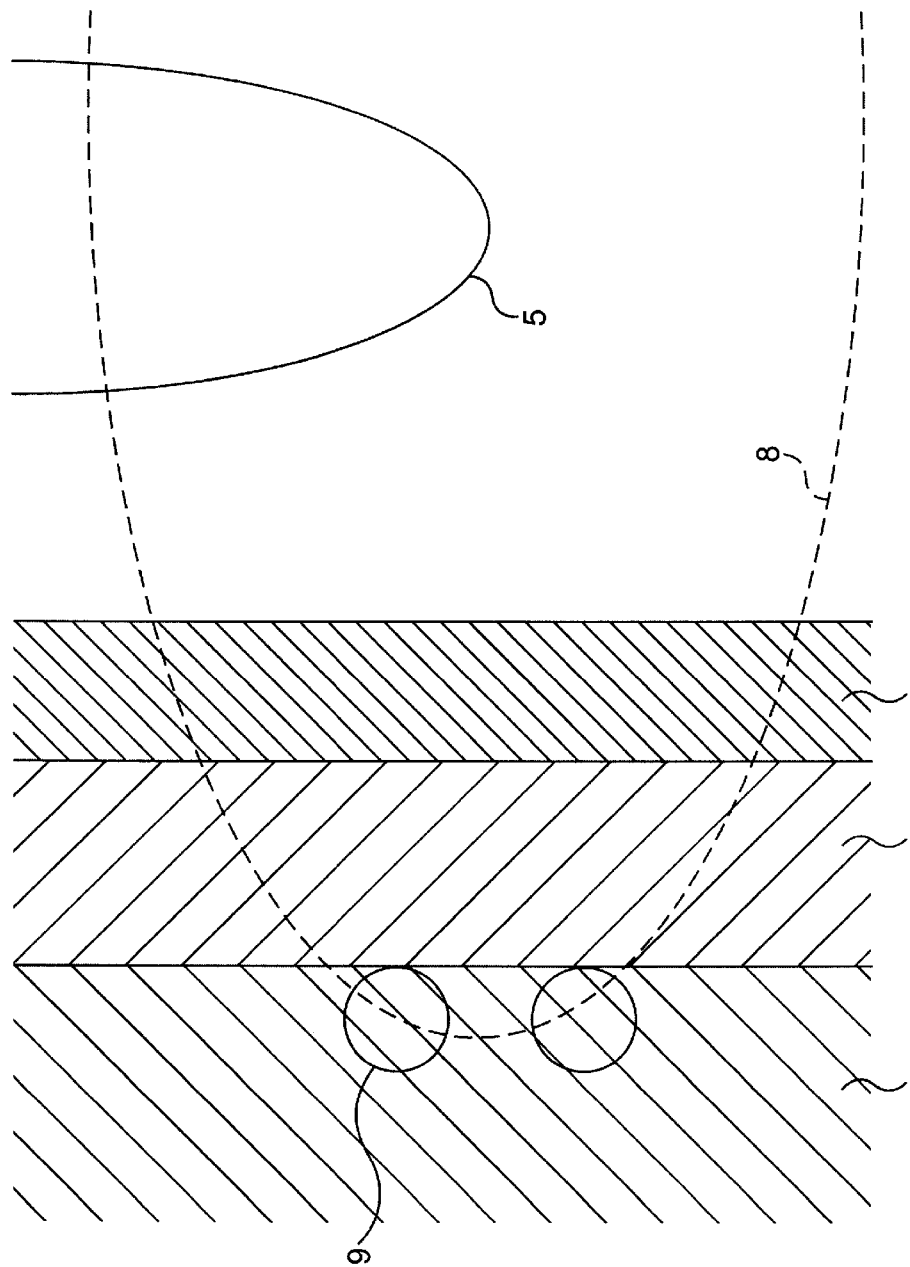
Figure 3:
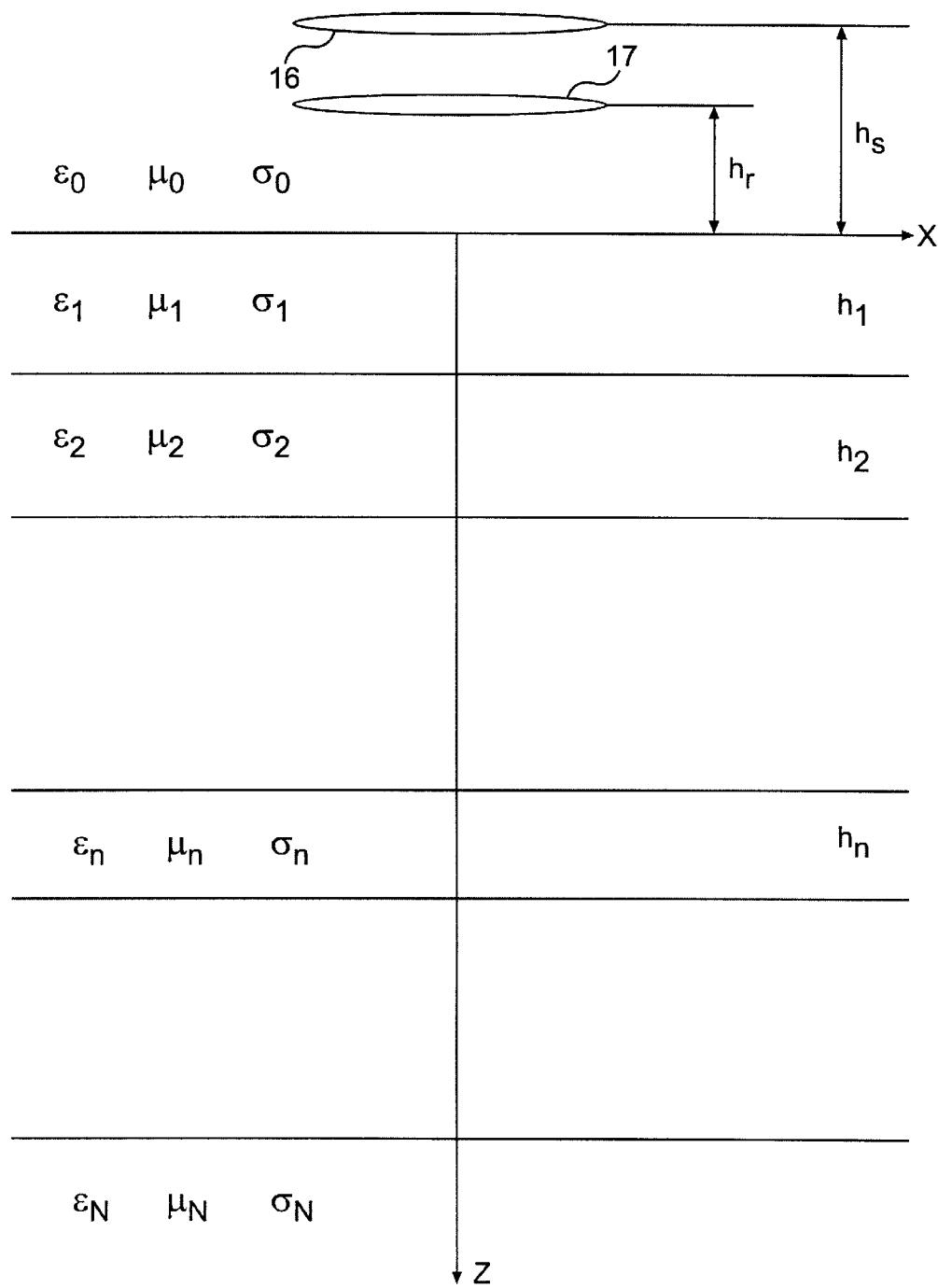
Figure 4:
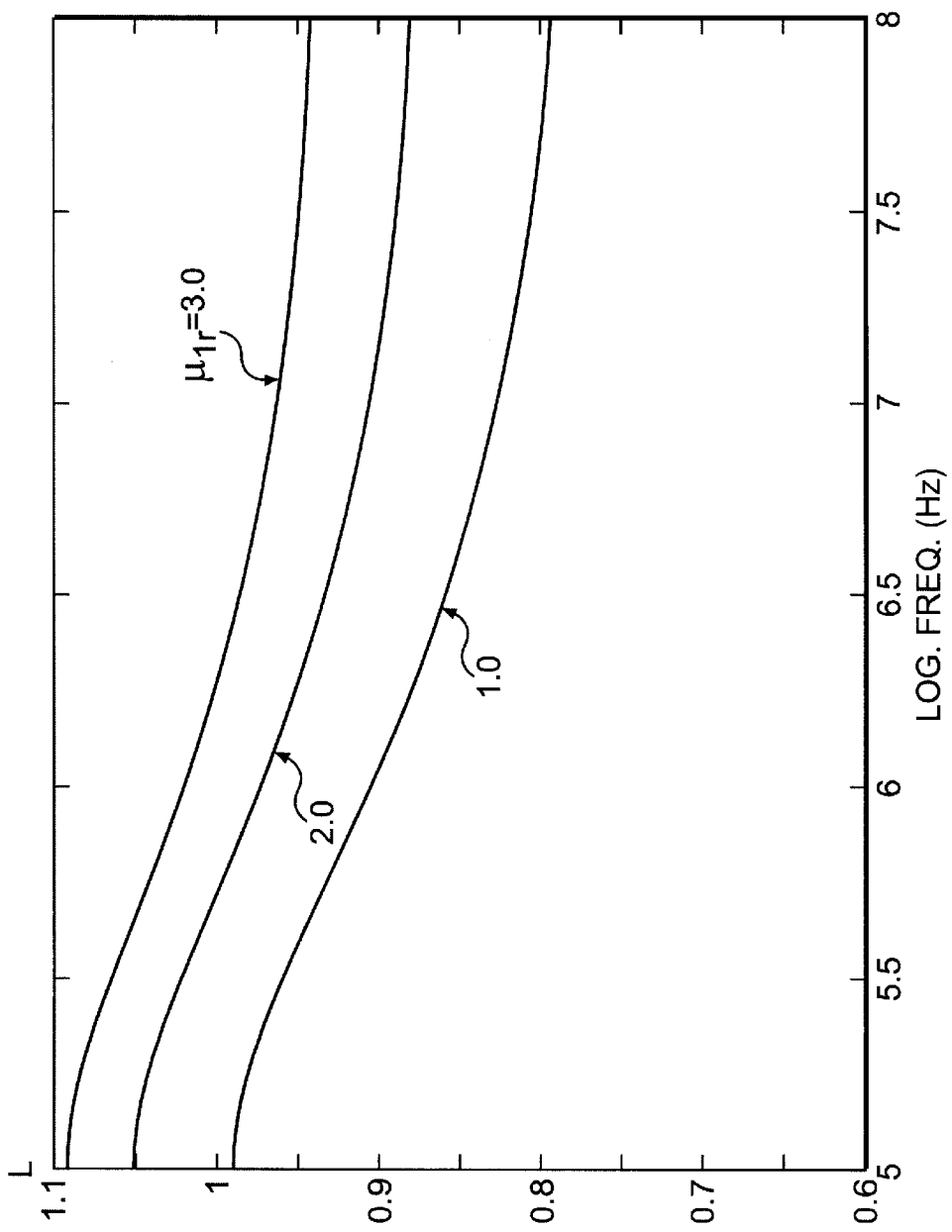
Figure 5:
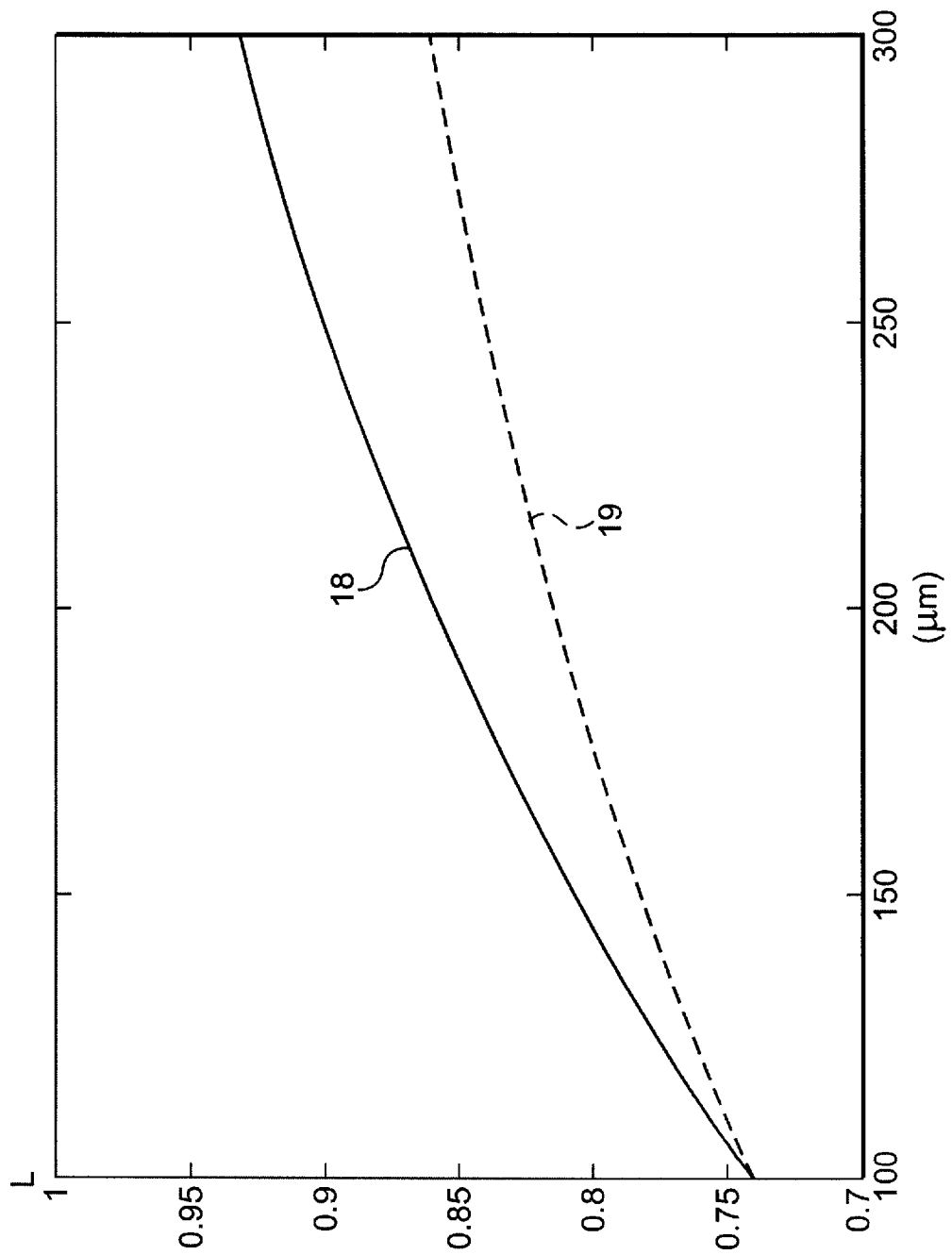
Figure 6:
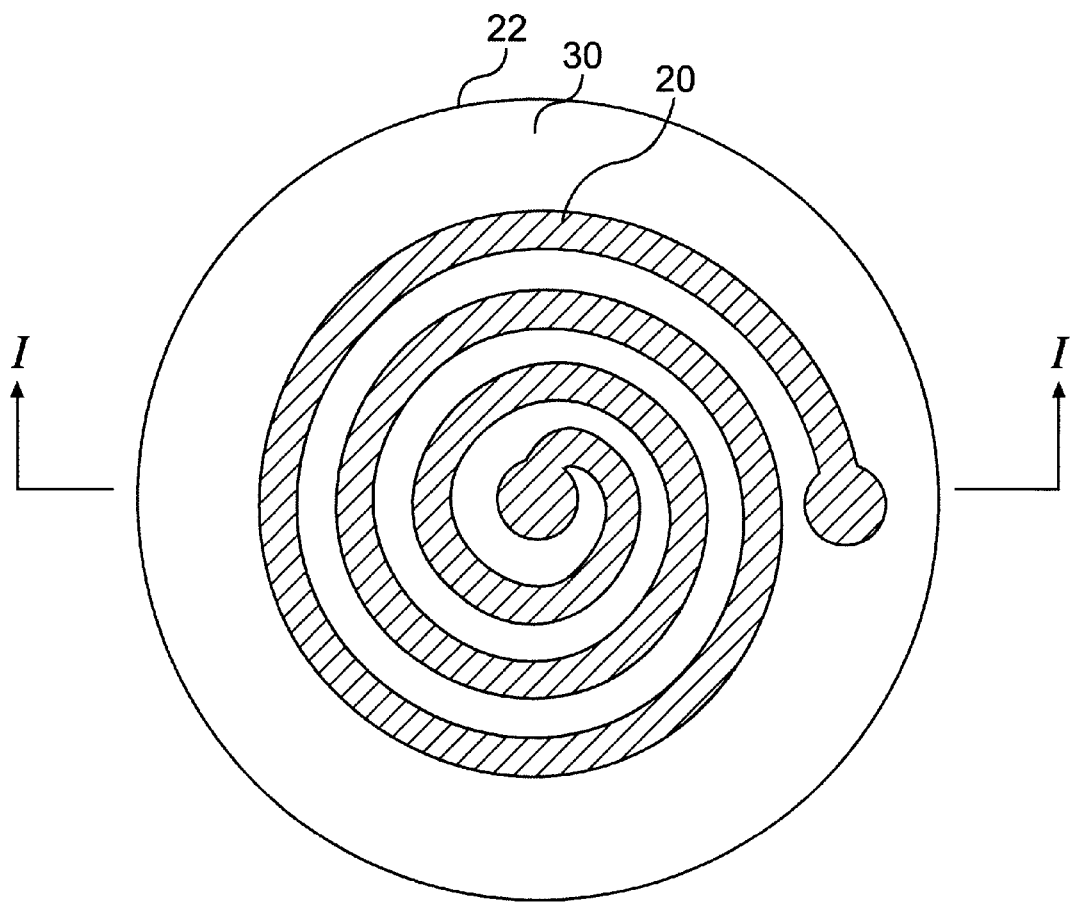
Figure 7:
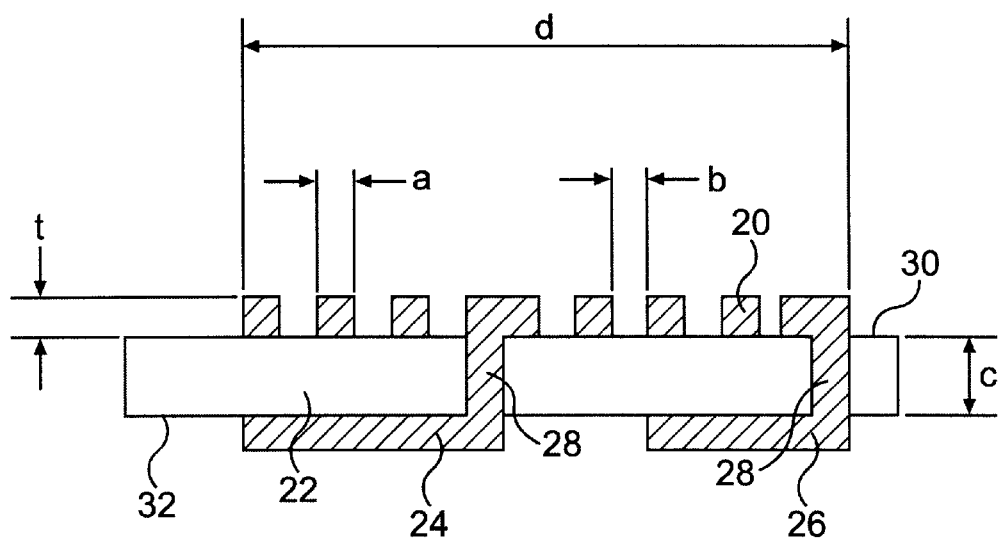

FIG. 1 is a simplified scheme illustrating the structure of a device by means of which a method according to the invention may be performed, FIG. 2 is a very simplified view illustrating the principle of the so-called eddy current method, FIG. 3 is a view illustrating equivalent coils and layers used in a mathematical inversion model, FIG. 4 is a diagram illustrating how the inductance of the measurement coil changes with the frequency of the alternating field at different values of the magnetic permeability of one of the layers, here the outermost of the layers in FIG. 3, FIG. 5 is a diagram illustrating how the inductance in said measurement coil for a given frequency changes with the distance of the measurement coil to the substrate for two different values of the magnetic permeability of one of the layers, here the outermost layer, FIG. 6 shows schematically a view of an electric measurement component which may be part of the method and the device according to the present invention, and FIG. 7 shows schematically a cross-sectional view of the electric measurement component which is shown in FIG. 6.

DETAILED DESCRIPTION OF A PREFERRED EMBODIMENT OF THE INVENTION

In order to illustrate the principle behind the present invention, an example will first be given of how the eddy current method is used for determining thickness such as is explained in the above-mentioned published Swedish application.

In FIG. 1 the structure of a device according to the mentioned document for determining the thickness of one or more layers arranged on each other on a substrate by the so-called EC-method (EC=eddy current) is schematically illustrated. In this case the thickness is measured of the oxide layer 1 which is formed on a substrate 2 in the form of a wall, consisting of a zirconium alloy, of a fuel rod 3, which is used in a nuclear reactor (see also FIG. 2). On the oxide layer 1 is in addition a so-called crud layer 4 arranged, which usually consists of a mixture of Fe, Zn and O, which may have a composition comparable to $ZnFe_2O_4$. The oxide layer is in the present case zirconium dioxide. Outside the layer 4, cooling water is intended to flow for cooling of the fuel rod walls heated by the cleavage of the fuel in the fuel rod. The device comprises a coil 5, which is formed by a filament of an electrically conductive material wound in turns in a layer, such that it is possible to describe the coil by a mathematical model, and this coil 5 is connectable to a unit 6 arranged to apply an alternating voltage of a variable frequency between its terminals 7. In this manner an electromagnetic alternating field, which is indicated by magnetic flux lines 8, may be produced via the coil 5. The coil 5 is intended to be brought to the immediate vicinity of the outermost 4 of the layers. Hereby the flux lines a of the alternating flux will pass through the layers, such as is illustrated very schematically in FIG. 2, and eddy currents will be produced in the electrically conductive layer 2 penetrated by the flux lines 8 essentially perpendicular to the flux lines in a manner known in electromechanics, which is indicated very schematically by the rings 9 (actually these currents are to be described by essentially larger eddy currents paths than those shown), wherein the thus obtained eddy current losses in the layer are proportional to inter alia the square of the thickness of the electrically conductive layer in the direction perpendicular to the magnetic flux lines and the current density in the layer. The thickness of the substrate does hereby usually not have any influence, since it is often so large that it may be considered as infinite. The eddy currents produced in this manner will retroact on the alternating field, such that the aspect of this field is dependent thereon. This influence will thereby be dependent on the distance between the coil 5 and the electrically conductive layer 2 and thus at a certain distance between the coil and the outer border of the layer 1 dependent on the thickness of the oxide layer 1. The electromagnetic properties, such as dielectric constant, electric conductivity and magnetic permeability, of the substrate and the different layers influence the character of the eddy currents and the retroaction on the alternating field. If, for example, some of the layers is magnetic, such as it is assumed in the present case concerning the crud layer 4, then this layer will partly neutralize the influence of the eddy currents on the alternating field, such that the alternating field, at measurement at a single frequency will get a similar aspect as if the crud layer had not been magnetic but the thickness of the oxide layer 1 had been essentially larger than what is actually the case.

The device also comprises means forming part of the unit 6 is and arranged to measure the alternating field and means for setting the frequency of the alternating field for performing said measurement at different frequencies within a wide frequency range, preferably extending over one or more orders of magnitude. Suitably frequencies between 100 kHz and 50 MHz are used. Said measurement is done by measuring the intensity of the current which flows through the coil 5 and the amplitude and the phase of the voltage across the coil 5, wherein with the phase is meant the phase of the voltage relative to the current through the coil. When it is assumed that the coil only couples inductively with the layers and the substrate, it may thus be expressed as if it is the inductance of the coil that is measured.

The device comprises an arrangement 10 arranged to calculate the thickness of the layer 1 or the layers 1 and 4 on the basis of information from said measurement and information about at least some of the electromagnetic properties of the substrate and the layer or layers. This arrangement receives measurement signals from the measurement arrangement 11. The calculation arrangement 10 comprises a composed mathematical model illustrated by a box 12, which is formed by a mathematical model 13 describing the coil 5 and a mathematical inversion model 14 described below. By the interaction of the mathematical models 13 and 14 a result is obtained in the form of layer thicknesses, which is indicated by the box 15. In practice the whole arrangement 10 is probably formed by a calculation computer.

The mathematical model for the coil is worked out to describe the coil in the form of an equivalent coil, and more precisely it describes the coil by two equivalent coils in the form of an emitter coil and a receiver coil, wherein thus the emitter coil has the characteristics concerning alternating field and similar which it would have in the absence of influence from the different layers and the substrate and the receiver coil has the characteristics which the coil obtains through said influence. In FIG. 3 is illustrated how in this manner the mathematical model describes the coil in the form of an emitter coil 16 and a receiver coil 17, which are positioned at the distance $h_s$ and $h_r$, respectively, from the outermost layer. Furthermore, in FIG. 3, the dielectric constant $\epsilon$, the magnetic permeability $\mu$ and the electric conductivity $\sigma$ are given as electromagnetic properties for each of the layers and for the cooling water outside the outermost layer and inside the innermost layer. These electromagnetic properties are introduced into said mathematical inversion model, which is used as a mathematical model concerning the constitution of the substrate and the layers and their influence on the alternating field generated by the coil. A theoretical value is calculated for the alternating field through the mathematical model for the coil and the mathematical inversion model and the result obtained from this calculation is compared with the result of the measurement of the alternating field, wherein the calculation thereby is done based on measurements at different frequencies, wherein in this calculation an assumed thickness for the layer in question is introduced into this model, whereafter a new value for said thickness is introduced into the mathematical inversion model and this procedure is repeated until essentially agreement has been obtained between the measured and calculated alternating field. In this way a very reliable result concerning the thicknesses of the different N+1=layers in FIG. 3 is obtained.

By determining the inductance of the receiver coil, the thicknesses of the different layers may thus be calculated by the introduction of the electromagnetic properties of the different layers. By using the measurement values from different frequencies and by introducing different frequencies into the calculation model, it may be determined how many layers there are and which thickness these have. For example, also the magnetic permeability of one or a few of the layers may thereby be unknown and determined through said calculations for different frequencies. It should however be mentioned, that it is also possible that the magnetic permeability of, for example, the crud layer 4 is unknown, but that this permeability is determined through separately provided means for measuring this permeability, such that this permeability may be introduced as a known quantity into the mathematical inversion model.

In FIG. 4 is illustrated how according to the mathematical inversion model a normalized inductance L of the receiver coil varies with the frequency for different assumed values of the relative magnetic permeability $\mu_1 r$ of the crud layer, wherein the relative magnetic permeability is set equal to 1 for a non-magnetic crud layer, i.e. the same value as it has in the oxide layer. From this figure is clear that the inductance of the coil is influenced considerably by a change of the magnetic permeability, and in FIG. 5 is illustrated the distance which it is arrived at that the coil has from the substrate at a given normalized inductance L for two different assumed values of the relative magnetic permeability. These values are thereby set to 1 and 2 (curve 18 and 19, respectively). From this is clear that in case it is disregarded that the crud layer is magnetic, but it appears that this is actually the case and that it should have a relative magnetic permeability of 2, then it would be concluded that the distance between the substrate and the coil is 270 $\mu$m at a determined inductance of 0.85, while the distance actually is 190 $\mu$m. Thereby 100 $\mu$m is the distance between the oxide layer and the coil, such that the difference in determined thickness of the oxide layer is 170 $\mu$m in relation to 90 $\mu$m.

The measurement of the resulting electromagnetic alternating field may be done by measuring the impedance of a receiver coil 5, positioned near the outermost layer, and the phase shift which a voltage over the receiver coil has in relation to a current through a coil 5, which is used for generating the alternating field. Said impedance and phase shift may be measured by measuring the intensity of the current through the coil which generates the alternating field and the amplitude and the phase angle of the voltage over the receiver coil 5 relative to said current.

According to the present invention, the method (and the device) according to said Swedish patent application may be further developed to be used to also determine hydride content.

Here below an embodiment of the invention will be described for determining the hydride content in cladding tubes for fuel rods of a nuclear plant. The invention is however not limited to this field of use, but may applied within any field where it is desired to determine the hydride content in a substrate which have one or more layers positioned on the substrate.

As has been described above, such a cladding tube may comprise a zirconium alloy. The material in the cladding tube in here below called substrate 2. On the Substrate 2 there may also be, as has also been described above, for example an oxide layer 1 and a crud layer 4.

It should be noted that the cladding tube (the substrate 2) does not necessarily consist of only one material. It is for example possible that it consists of different layers with different zirconium alloys for optimizing the properties of the material. The substrate 2 mentioned in the following and in the claims may thus comprise more than one material. Even other materials than zirconium alloys may be used. The substrate 2 comprises however usually a methal which is electrically conductive. As an example below, zirconium is described as the substrate 2.

As has been described above, zirconium may combine with hydrogen to zirconium-hydrogen compounds. The electric conductivity is thereby impaired. There is thus a relationship between the electric conductivity of the substrate and the hydride content in the same.

The above-described iterative calculation model is now used to determine the hydride content. Certain known or predetermined parameters are thereby introduced into the model while unknown, free parameters are determined by the calculation. The known or predetermined parameters do not need to be known to their exact value. Sufficient accuracy is obtained if approximate values are known. For example, the following parameters may be used as known parameters in the calculation: the electric conductivity, the dielectric constant and the magnetic permeability of the oxide layer 1 and the crud layer 4 and the dielectric constant and the magnetic permeability of the substrate 2. Furthermore, the oxide layer 1 and the crud layer 4 may in certain applications be considered to have similar electrical and magnetical properties. It is therefore possible to consider these layers as one layer. The layers are often not electrically conductive or have a, relative to the substrate 2, low electric conductivity. In order to simplify the model, these layers (or this combined layer) may, compared to the substrate 2, be considered to be electrically insulating and non-magnetic. The free parameters which are determined may be the thickness of the oxide and the crud layer 1, 4 (or the combined thickness if these layers are considered as one layer) and the electric conductivity (and thereby the hydride content) of the substrate 2. It should be noted that in certain applications it may not be assumed that the oxide layer 1 and the crud layer 4 have similar electric and magnetic properties. For example, it is possible that zinc is injected into the reactor of a nuclear plant for obtaining a controlled water chemistry. In this case, the crud layer 4, may normally not be considered as being non-magnetic.

As has been described above, an electromagnetic alternating field is applied by means of the coil 5 and the resulting alternating field, which is formed by said interaction of the applied field and the field produced by the eddy currents, is measured. The measurement is done at different frequencies of the applied field.

The calculation is done through the above-described iterative method. I.e. assumed values of the free parameters are introduced into the calculation model and a resulting combined electromagnetic alternating field is calculated. The result of the calculation is compared with the result of the measurement. The free parameters are changed and the calculation is done again. This iterative process is performed until the calculated field corresponds to the measured field. In this manner, the free parameters may be determined, which in this example are the thickness of the oxide and the crud layers and the electric conductivity of the substrate.

With the help of the determined electric conductivity of the substrate, the hydride content is then determined. This may for example be done by calibrating against hydrogenated cladding tubes. That is, different cladding tubes of the same material as those which are to be tested have been exposed to hydrogen such that different hydrogen contents have been obtained. The electric conductivity and the hydride content have then been determined in known manners. The hydride content may for example be determined by neutron radiography or other known metallographic methods. In this manner, a relationship between the conductivity and the hydride content is obtained. This relationship may then for example be stored in a memory in the calculation arrangement 10. This relationship is thus used to determine the hydride content from the calculated conductivity of the substrate.

Instead of this calibration method, the hydride content as a function of the electric conductivity may also be calculated by means of a theoretical model.

With the present invention it is thus possible to determine the hydride content in the substrate 2 even if the thickness of the layers 1, 4 which are positioned on the substrate are not known. This makes it possible to measure the hydride content on location in a nuclear plant (for example in a fuel pool) without destroying the fuel rods. Expensive and complicated methods where the fuel rods must be taken away from the nuclear plant and analyzed at another location are thereby avoided.

With the method and the device according to the invention, both the hydride content in the substrate and the thickness of the oxide layer may be determined through one and the same measurement procedure. Alternatively, both the hydride content in the substrate and the combined thickness of an oxide layer and a crud layer may be determined through one and the same measurement procedure. Furthermore, it has been shown that said hydride content and thickness may be determined in a quick and simple manner and with a high accuracy.

In certain cases, the crud layer may be magnetic. By means of the present invention, the presence of such a magnetic crud layer may be detected. That is, with the method and the device according to the invention, wherein measurement is done at several different frequencies, the presence of a magnetic crud layer may be distinguished from, for example, a measurement result which depends on hydrides in the substrate.

For the generation and the detection of the electromagnetic alternating fields, different kinds of known coils may for example be used. It has however appeared that a particularly accurate result is obtained if the measurement is done with a particular kind of measurement component comprising a coil. It should be noted that different coils may be used as emitter and receiver coils. However, preferably the same coil is used as emitter and receiver coil.

An embodiment of this particular kind of measurement component is shown in the FIGS. 6 and 7. FIG. 7 is a cross-sectional view of the cross-section which has been marked with I in FIG. 6.

The measurement component comprises a coil. The coil comprises at least a first spiral-shaped part 20 which along essentially its full length is tangent to an essentially plane boundary surface.

In the shown embodiment, the coil has only one spiral-shaped part 20. The spiral-shaped part 20 thus in this embodiment forms the complete coil. The coil is positioned on a support member 22. This support member 22 is here below also called the substrate. The substrate 22 has a first side 30 and a second side 32. The coil is in this case thus positioned on the first side 30 of the substrate 22. The coil is formed in an electrically conductive material. This material may for example be copper or aluminium, but also other electrically conductive materials may be used. The coil, or the first spiral-shaped part 20, may have a thickness t which is chosen according to the circumstances. It is often suitable that this thickness t is between 1 $\mu$m and 100 $\mu$m. In particular a thickness t of between 20 $\mu$m and 50 $\mu$m has been shown to be suitable. A typical such thickness t is about 35 $\mu$m.

The coil according to the schematically shown embodiment in FIG. has about 3.5 turns of winding. The number of turns of winding depends on the field of use. For certain applications it may be suitable to have a higher number of turns of winding, for example 10–40 turns of winding. It is however often an advantage to make the coil as small as possible. It may thereby be suitable that the coil has about 4–10 turns of winding.

The electrically conductive material which forms the coil is hereafter called the wire. The width a of the wire may also vary depending on the field of use of the coil and depending on the method of production. A suitable value of the width a of the wire may be for example 30 $\mu$m–100 $\mu$m. It has been shown to be particularly suitable if the wire has a width a of about 70 $\mu$m. Also the distance between the turns of winding of the wire (which distance is marked with b) depends on the circumstances. A suitable such distance b may be about the same as the width a of the wire, i.e. it may often be suitable that this distance b is about 70 $\mu$m. The diameter d of the coil may also be chosen depending on the field of use of the coil. It is often suitable that this diameter d is less than 50 mm. For certain applications, for example concerning measurement of cladding tubes for fuel rods (which is described below) it has appeared to be suitable that the diameter d of the coil is less than 6 mm, and preferably less than 4 $\mu$m.

The substrate 22 may be formed of different suitable insulating materials. Polyimide is such a suitable material. The thickness c of the substrate 22 may vary. The thickness c of the substrate 22 may for example be less than 30 $\mu$m, preferably less than 20 μm, most preferably about 12 μm. Such a substrate may for example consist of polyimide.

The substrate 22 may be provided with through-openings 28 (so-called vias). These openings 28 may be used for connecting the spiral-shaped part 20 to contact sections 24, 26 positioned on the other side 32 of the substrate 22. Through these contact sections 24, 26, the coil may thus be connected to for example a device for generating an electromagnetic alternating field or to a detection device for detecting for example the voltage or the current over the coil.

According to the described embodiment, the first spiral-shaped part 20 (i.e. in this case the coil) is positioned essentially in a plane. This may be expressed as if the first spiral-shaped part 20 along essentially its full length is tangent to an essentially plane boundary surface. Such a boundary surface may for example constitute one side 30 of the substrate 22 itself or the boundary surface may be considered to constitute a plane which is tangent to the side of the spiral-shaped part 20 which is positioned on top in FIG. 7. As has been mentioned above, such a boundary surface is essentially plane. But when the coil is to be used for measuring a bent measurement object it may be advantageous if said boundary surface has a curvature which corresponds to the curvature of such a measurement object.

Although not shown in the figures, it is possible that the electric measurement component in addition to a first spiral-shaped part 20 also comprises a second spiral-shaped part positioned on the other side 32 of the support member 22. The second spiral-shaped part may suitably be displaced relative to the first spiral-shaped part 20 such that the electrically conductive turns of winding of the second spiral-shaped part are positioned at positions corresponding to the spaces between the electrically conductive turns of winding of the first spiral-shaped part 20. The first 20 and the second spiral-shaped parts may be electrically connected to each other. The connection may be formed by a so-called via through the substrate 22. The two spiral-shaped parts may thus together form a coil. Each of the spiral-shaped parts is suitably along essentially its full-length tangent to an essentially plane boundary surface in a similar manner as in the shown embodiment. An advantage with the fact that the coil comprises two such spiral-shaped parts is that the coil may be made small (have a small diameter) but may still comprise a sufficient number of turns of winding for obtaining a good inductive coupling with the measurement object.

It should be noted that the two spiral-shaped parts may also be separated from each other (i.e. not electrically connected to each other). According to such an embodiment, each of the spiral-shaped parts should thus have contact sections for connection to a device for generating an electromagnetic alternating field or to a detector.

Although not shown in the figures, it is possible that the spiral-shaped part or parts are covered by a protective electrically insulating layer of a suitable material.

Independently of whether the coil comprises one or more spiral-shaped parts, it is the case that the coil essentially does not comprise any helically-shaped part of any importance.

The electrical measurement component may be produced in different manners which are known in connection with for example circuit card or semi-conductor production.

As has been mentioned above, the coil may be described by a simplified model where the coil for example is described as if it comprised only one turn of winding, or as if it comprises several turns of winding positioned in a plane.

The present invention is not limited to the shown embodiments but may be varied and modified within the scope of the following claims.

What is claimed is:

1. A method for determining hydride content in an electrically conductive substrate of a measurement object, the method comprising the following steps:
generating a first electromagnetic alternating field by means of a coil positioned in the immediate vicinity of the measurement object, wherein said coil comprises an electrically conductive material and comprises at least a first spiral-shaped part that along essentially its full length is tangent to an essentially planar boundary surface, wherein said first electromagnetic alternating field at least partly penetrates the substrate and creates in the substrate eddy currents that produce a second electromagnetic alternating field that retroacts on the first electromagnetic alternating field;
setting said first electromagnetic alternating field at at least two different frequencies;
measuring, at said frequencies, a combined electromagnetic alternating field that is formed by the interaction of said first and second electromagnetic alternating fields;
determining the hydride content in said substrate by using data that have been obtained through said measuring step and information about at least some of the electromagnetic properties of the measurement object, wherein said determining step involves using a mathematical model which describes said coil, or a simplified model of said coil, and the constitution of the measurement object and the influence of the measurement object on said first electromagnetic alternating field, wherein said determination comprises a calculation of a resulting combined electromagnetic alternating field in response to said generated first electromagnetic alternating field, which calculation comprises the introduction of predetermined or known values for at least some of the electromagnetic properties of said measurement object and the assumption of one or more free parameters of said measurement object and wherein said determination comprises an iterative process according to which the assumed free parameter or parameters are changed until said measured combined electromagnetic field corresponds to said calculated combined electromagnetic field.

2. The method according to claim 1, wherein the measurement object comprises at least one layer positioned on the substrate.

3. The method according to claim 2, further comprising:
determining the thickness of at least one of said layer or layers positioned on the substrate, wherein determining the thickness comprises using data that have been obtained through said measurement and information about at least some of the electromagnetic properties of the substrate or the layers.

4. The method according to claim 1, further comprising:
determining the electric conductivity of the substrate, wherein from this determination the hydride content is determined.

5. The method according to claim 1, wherein the measurement object comprises a structural member in a nuclear plant.

6. The method according to claim 5, wherein said substrate is the material of the structural member and wherein there is an oxide layer and a crud layer on said substrate.

7. The method according to claim 1, wherein the measurements of the alternating field are performed over a wide frequency range extending over one or more orders of magnitude.

8. The method according to claim 7, wherein said frequency range at least covers the frequencies between 500 kHz and 50 MHz.

9. A device for determining hydride content in an electrically conductive substrate of a measurement object, the device comprising:

a coil operable to generate a first electromagnetic alternating field in the immediate vicinity of the measurement object, the coil comprising a electrically conducting material and comprises at least a first spiral-shaped part that along substantially its full length is tangent to a substantially planar boundary surface, the alternating field at least partly penetrates the substrate and in this substrate creates eddy currents which in their turn produce a second electromagnetic alternating field which retroacts on the first electromagnetic alternating field;

means for setting the first electromagnetic alternating field at at least two different frequencies;

means for measuring, at said frequencies, a combined electromagnetic alternating field that is formed by the interaction of the first and the second electromagnetic alternating fields; and an arrangement arranged for determination of the hydride content in the substrate by using data which have been obtained through said measurement and information about at least some of the electromagnetic properties of the measurement object, wherein said arrangement is arranged such that said determination is performed by means of a model that describes said coil or a simplified model of said coil and the constitution of the measurement object and the influence of the measurement object on the first electromagnetic alternating field, wherein said arrangement is arranged such that the determination comprises a calculation of a resulting combined electromagnetic alternating field in response to said generated first electromagnetic alternating field, wherein the arrangement comprises means for introducing predetermined or known values for at least some of the electromagnetic properties of the measurement object, wherein the arrangement comprises means for introducing one or more free parameters of the measurement object, and wherein the arrangement is arranged such that said determination comprises an iterative process according to which the assumed free parameter or parameters are changed until the measured combined electromagnetic field corresponds to the calculated field.

10. The device according to claim 9, wherein the free parameters comprise the electric conductivity of the substrate and the thickness of the layer or layers positioned on the substrate.

11. The device according to claim 9, wherein the arrangement is arranged such that also the thickness of at least one layer or layers positioned on the substrate is determined by using data that have been obtained through said measurement and information about at least some of the electromagnetic properties of the substrate or the layers.

12. The device according to claim 9, wherein the arrangement is arranged such that the electric conductivity of the substrate is determined and such that from this determination the hydride content is determined.

13. The device according to claim 9, arranged such that the measurements of the alternating field are performed over a wide frequency range extending over one or more orders of magnitude.

14. The device according to claim 9, wherein the arrangement comprises means for introducing predetermined or known values of layers positioned on the substrate.

* * * * *